Figure 1:
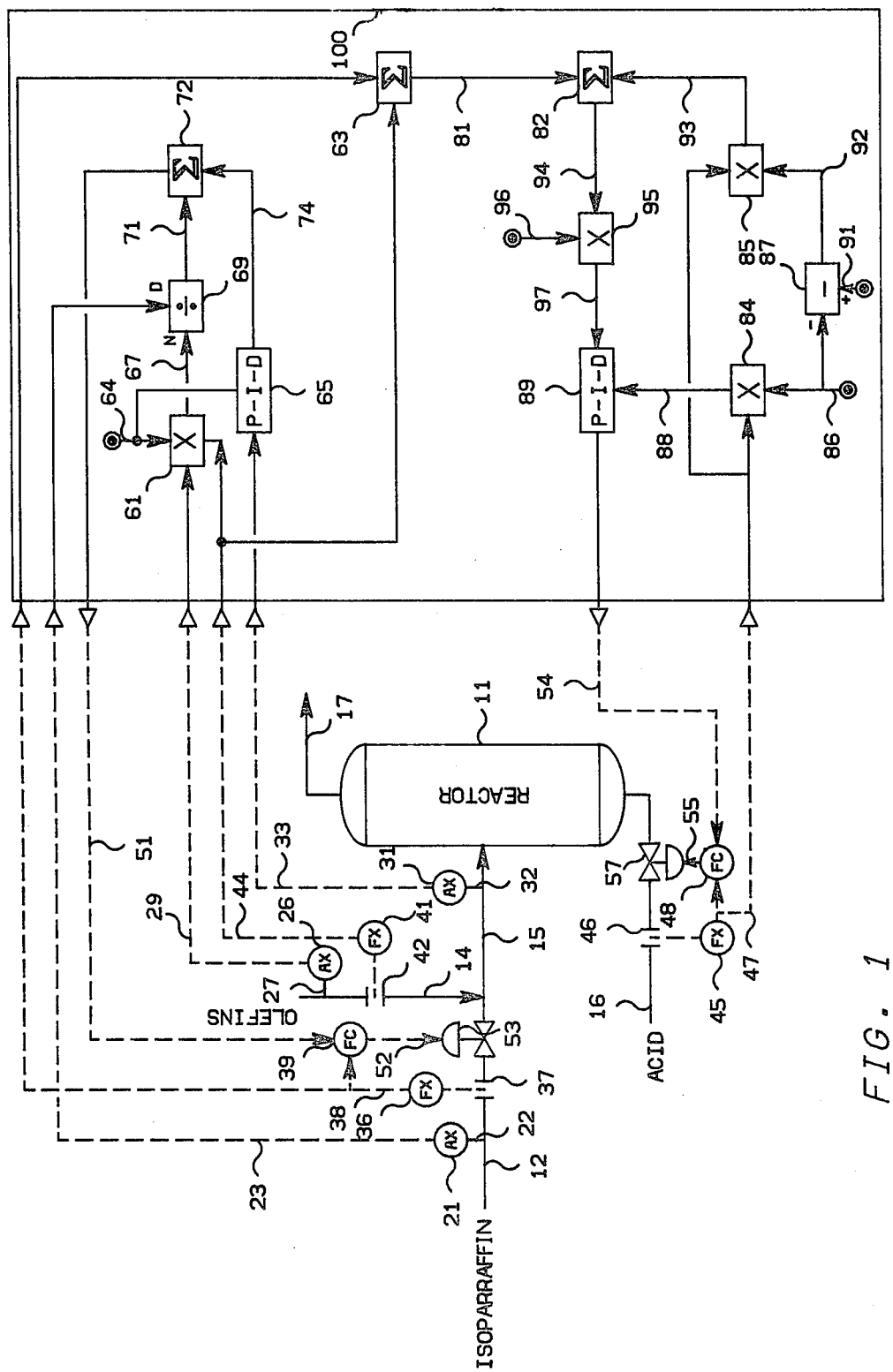

United States Patent [19]

Funk et al.

[11] Patent Number: 4,482,969

[45] Date of Patent: Nov. 13, 1984

[54] CONTROL OF AN ALKYLATION REACTOR

[75] Inventors: Gary L. Funk; James A. Feldman, both of Bartlesville, Okla.

[73] Assignee: Phillips Petroleum Company, Bartlesville, Okla.

[21] Appl. No.: 356,594

[22] Filed: Mar. 9, 1982

[51] Int. Cl.$^3$ .............................................. G06F 15/46
[52] U.S. Cl. .................................... 364/500; 364/510; 422/62; 585/701
[58] Field of Search .............. 564/499, 500, 502, 510; 422/62, 67; 585/701

[56] References Cited

U.S. PATENT DOCUMENTS

| | | | |
|---|---|---|---|
| 3,002,818 | 10/1961 | Berger | 23/253 |
| 3,080,438 | 3/1963 | Sailors | 260/683.48 |
| 3,108,094 | 10/1963 | Morgan | 364/500 |
| 3,614,682 | 10/1971 | Smith | 364/500 |
| 3,729,624 | 4/1973 | Hopkins et al. | 364/500 |
| 3,814,915 | 6/1974 | Sweeney, Jr. | 364/500 |
| 3,826,904 | 7/1974 | Leonard et al. | 364/502 |
| 3,864,346 | 2/1975 | Child et al. | 585/701 |
| 3,981,942 | 9/1976 | Zabransky | 585/701 |
| 4,249,908 | 2/1981 | Funk | 364/500 |
| 4,288,230 | 9/1981 | Ebeling et al. | 364/500 |
| 4,317,795 | 3/1982 | Makovec et al. | 422/62 |
| 4,332,590 | 6/1982 | Smith | 364/500 |

Primary Examiner—Jerry Smith
Assistant Examiner—John R. Lastova
Attorney, Agent, or Firm—French and Doescher

[57] ABSTRACT

An acid alkylation process is controlled so as to maintain a desired ratio of isobutane to olefins in a fluid stream flowing to the alkylation reactor and to maintain a desired acid to hydrocarbon ratio in the alkylation reactor. Also, if parallel alkylation reactors are utilized, the flow rate of the olefin stream to one of the alkylation reactors is manipulated so as to maintain a balanced loading on the parallel alkylation reactors. Such control results in improved quality of the alkylate produced and also improves the amount of alkylate produced from a particular amount of fluid to the alkylation reactor.

34 Claims, 2 Drawing Figures

CONTROL OF AN ALKYLATION REACTOR

This invention relates to acid alkylation. In one aspect, this invention relates to control of the olefin to isoparaffin ratio in the feed stream flowing to an alkylation reactor. In another aspect, this invention relates to control of the acid to total hydrocarbon ratio in the alkylation reactor. In still another aspect, this invention relates to the balancing of the load on two or more parallel alkylation reactors.

Alkylation is a process to combine at least one isoparaffin such as isobutane with an olefin such as propylene, butylenes or amylenes to produce a liquid with superior stability and antiknock quality suitable for blending aviation gasoline and motor fuel. An acid catalyst such as hydrofluoric (HF) acid or sulfuric acid serves to catalyze the reaction.

The isoparaffin commonly alkylated is isobutane although isopentane could be utilized if desired. The most commonly used olefins are propylene and butylenes with amylenes being used less frequently. As used herein, the term butylenes refers to 1-butene, cis-2-butene, trans-2-butene and isobutylene. As used herein the term amylenes refers to all of the five carbon olefins. Some propane and normal butane may also be present with the propylene and butylenes, and some propane and isopentane may be produced in the alkylation.

The present invention is not dependent on the particular olefin feedstock utilized and thus, for the sake of convenience, this particular feed stream will simply be referred to as an olefin feed stream. In like manner, since the most commonly used isoparaffin is isobutane, the isoparaffin referred to will be isobutane. Also, the acid referred to will be HF acid even though other acids could be utilized if desired.

As with any process, it is desirable to improve the quality of the product of an alkylation process. Generally, the octane number of the alkylate is the criterion utilized to judge the quality of the product from the alkylation process. Also, it is desirable to be able to improve the amount of product produced from a particular amount of feed in an alkylation process.

Close control of the alkylation reactor is necessary in order to accomplish the above objectives. Of particular interest in such control is the isobutane to olefin ratio in the feed flowing to the alkylation reactor and the acid to total hydrocarbon ratio in the reactor. Further, when two or more alkylation reactors are in a parallel configuration, it is desirable to be able to balance the load on the two or more parallel reactors so as to accomplish the above objectives.

It is thus an object of this invention to provide control of an alkylation reactor so as to maintain a desired olefin to isobutane ratio in the feed stream flowing to the alkylation reactor and maintain a desired acid to total hydrocarbon ratio in the alkylation reactor. It is also an object of this invention to control two or more alkylation reactors in parallel so as to balance the load on the two or more alkylation reactors in parallel.

In accordance with the present invention, control of an alkylation process in which an olefin-containing stream is combined with an isobutane stream with the combined stream being supplied to the alkylation reactor is accomplished by manipulating the flow rate of the isobutane stream so as to maintain a desired ratio of isobutane to olefins in the combined stream. Also, in accordance with the present invention, method and apparatus is provided for manipulating the flow rate of the acid stream to the alkylation reactor so as to maintain a desired acid to hydrocarbon ratio in the alkylation reactor. Finally, in accordance with the present invention, in an alkylation process in which parallel alkylation reactors are utilized, the flow rate of the olefin stream to one of the alkylation reactors is manipulated so as to maintain a balanced loading on the parallel alkylation reactors.

In general, control of the isobutane feed stream so as to maintain a desired isobutane to olefin ratio in the combined stream is accomplished by determining the total flow of isobutane required to maintain the desired isobutane to olefin ratio based on an analysis of the olefin-containing feed stream, the flow rate of the olefin-containing feed stream and the desired isobutane to olefin ratio in the combined feed stream. The thus determined value is utilized to determine the desired flow rate of the isobutane stream.

In general, the control of the flow rate of the acid stream is accomplished by first determining the amount of acid and hydrocarbons in the acid stream. It is noted that the acid stream may contain as much as 80% hydrocarbons. After this determination is made, the amount of hydrocarbons in the acid stream is summed with the amount of hydrocarbons in the combined stream flowing to the alkylation reactor to determine the total hydrocarbons being provided to the alkylation reactor. This total hydrocarbons is utilized to determine the desired acid flow rate with a comparison of the desired acid flow rate and actual acid flow rate being utilized to manipulate the flow rate of the acid stream.

In general, balancing of the load on parallel reactors by controlling the flow rate of olefins to one of the reactors is accomplished by determining the flow rate of olefins to one of the reactors required to maintain the temperature of the reactants removed from each of the parallel reactors substantially equal. This flow rate is utilized to manipulate the flow rate of olefins to one of the reactors in parallel.

Figure 2:
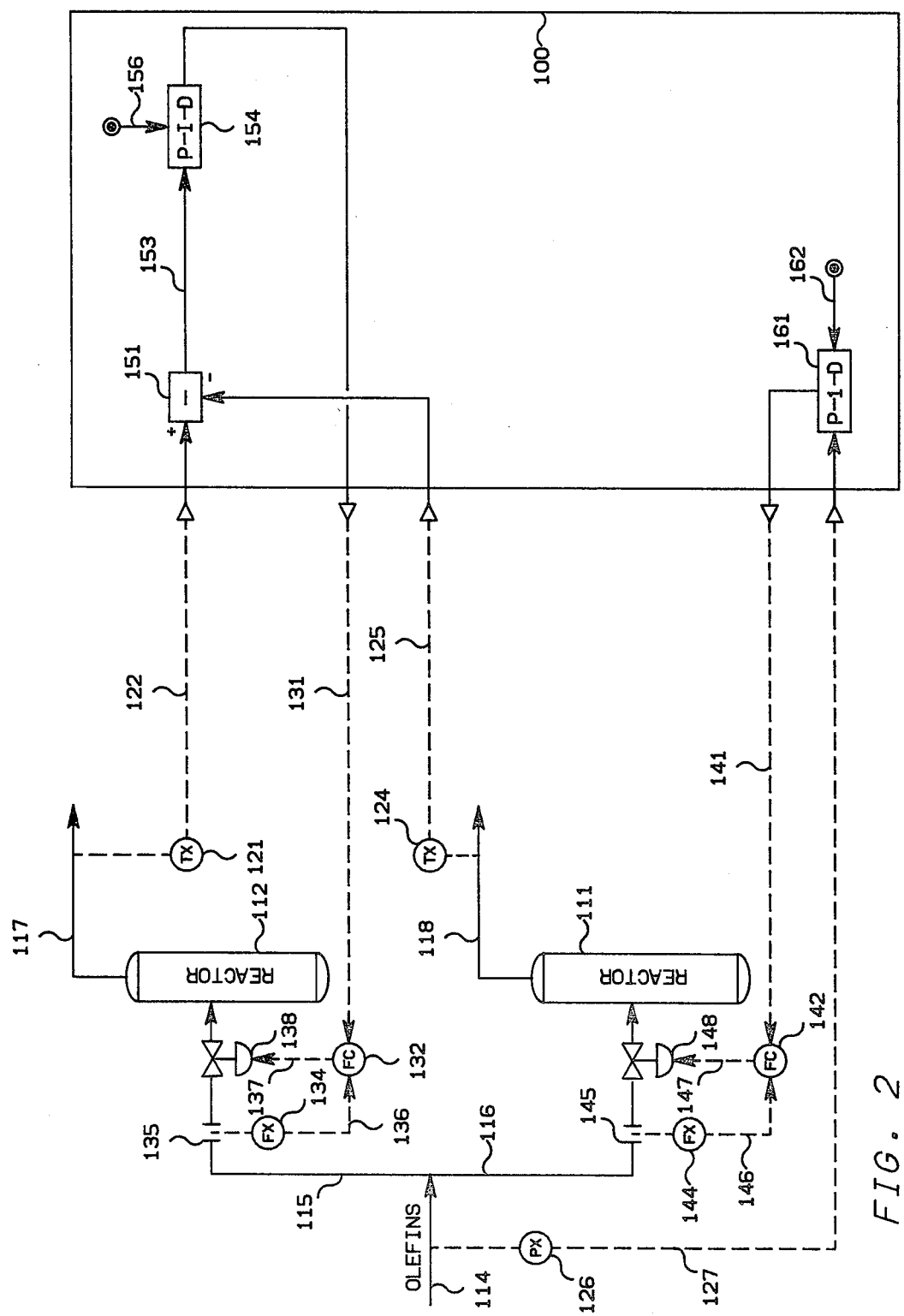

Other objects and advantages of the invention will be apparent from the foregoing brief description of the invention and the claims as well as the detailed description of the drawings in which:

FIG. 1 is a diagrammatic illustration of an alkylation reactor together with the associated isobutane to olefin ratio and acid to hydrocarbon ratio control system of the present invention; and FIG. 2 is a diagrammatic illustration of two alkylation reactors in parallel together with the associated control system of the present invention for maintaining a balanced loading on the two parallel alkylation reactors.

The invention is illustrated in terms of a very simple alkylation reactor configuration in which the olefin and isobutane feed streams are combined and provided to the alkylation reactor separately from the acid stream. In some alkylation reactors, the olefin and isobutane combined stream may be combined with the acid stream before being provided to the alkylation reactor. The invention is not limited to any particular alkylation reactor configuration but is rather applicable to any alkylation reactor in which it is possible to control the flow rate of the various streams.

A specific control system configuration is set forth in FIG. 1 for the sake of illustration. However, the invention extends to different types of control system configurations which accomplish the purpose of the invention.

Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that if a flow is measured in pneumatic form it must be transduced to electrical form if it is to be transmitted in electrical form by a flow transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

A digital computer is used in the preferred embodiment of this invention to calculate the required control signal based on measured process parameters as well as set points supplied to the computer. Analog computers or other types of computing devices could also be used in the invention. The digital computer is preferably an OPTROL ® 7000 Process Computer System from Applied Automation, Inc., Bartlesville, Okla.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

The controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to the drawings, and in particular to FIG. 1, there is illustrated an alkylation reactor 11. A feed stream containing an isoparaffin (the isoparaffin is referred to hereinafter as isobutane) flowing through conduit means 12 and a feed stream containing olefins flowing through conduit means 14 are combined and provided to the reactor 11 through conduit means 15. An acid containing stream (the acid is referred to hereinafter as HF acid) is provided to the reactor 11 through conduit means 16. Reactants are removed from the reactor 11 through conduit means 17.

The reactor configuration illustrated in FIG. 1 is a typical reactor configuration. For the sake of convenience in illustrating the invention, only a very basic reactor configuration has been illustrated. Other process streams which might be provided to or withdrawn from the reactor 11, additional process equipment such as pumps, heat exchangers, etc. and additional control components which might be associated with the alkylation reactor have not been illustrated since such additional features do not play any part in the description of the present invention.

Essentially, a number of process measurements are made with the values of these process measurements being provided to a digital computer. In response to the process measurements and operator supplied set points, the digital computer provides two output control signals which are utilized to manipulate the isobutane to olefin ratio in the feed stream flowing through conduit means 15 and the acid to hydrocarbon ratio in the reactor 11. The process measurements will first be described and then the manner in which the control signals are utilized to control the alkylation reactor will be described. Thereafter, a detailed description of the manner in which the process measurements are utilized to derive the control signals will be provided.

Analyzer transducer 21, which is preferably a chromatographic analyzer such as the OPTICHROM® 2100 Computer Chromatograph System from Applied Automation, Inc., Bartlesville, Okla. is in fluid communication with conduit means 12 through conduit means 22. Analyzer transducer 21 provides an output signal 23 which is representative of the percentage of isobutane which is contained in the feed stream flowing through conduit means 12. Typically, the isobutane feed stream will have impurities such as butanes and propane. Signal 23 is provided from the analyzer transducer 21 as an input to computer 100.

In like manner, analyzer transducer 26, which is also preferably a chromatographic analyzer, is in fluid communication with conduit means 14 through conduit means 27. Analyzer transducer 26 provides an output signal 29 which is representative of the percentage of the feed stream flowing through conduit means 14 which is olefins. Again, as in the case of the isobutane feed stream, the olefin containing stream flowing through conduit means 14 may not be completely made up olefins. Signal 29 is provided from the analyzer transducer 26 as an input to computer 100.

Analyzer transducer 31, which is also preferably a chromatographic analyzer, is in fluid communication with conduit means 15 through conduit means 32. Analyzer transducer 31 provides an output signal 33 which is representative of the actual isobutane to olefin ratio in the feed stream flowing through conduit means 15. Signal 33 is provided from the analyzer transducer 31 as an input to computer 100.

Flow transducer 36 in combination with the flow sensor 37, which is operably located in conduit means 12, provides an output signal 38 which is representative of the actual flow rate of the feed stream flowing through conduit means 12. Signal 38 is provided from the flow transducer 36 as the process variable input to the flow controller 39 and as an input to computer 100. In like manner, flow transducer 41 in combination with the flow sensor 42, which is operably located in conduit means 14, provides an output signal 44, which is representative of the actual flow rate of the feed stream through conduit means 14, to computer 100.

Flow transducer 45 in combination with the flow sensor 46, which is operably located in conduit means 16, provides an output signal 47 which is representative of the flow rate of the acid containing stream flowing through conduit means 16. Signal 47 is provided as the process variable input to the flow controller 48 and is also provided as an input to computer 100.

As has been previously stated, computer 100 provides two output control signals in response to the described process measurements and set points provided by an operator. Signal 51, which is provided from computer 100 as a set point signal to the flow controller 39, is representative of the flow rate of the isobutane-containing stream flowing through conduit means 12 required to maintain a desired isobutane to olefin ratio in the feed stream flowing through conduit means 15. In response to signals 51 and 38, the flow controller 39 provides an output signal 52 which is responsive to the difference between signals 51 and 38. Signal 52 is scaled so as to be representative of the position of the control valve 53, which is operably located in conduit means 12, required to maintain the actual flow rate of the isobutane containing stream flowing through conduit means 12 substantially equal to the desired flow rate represented by signal 51. Signal 52 is provided from the flow controller 39 as a control signal to the control valve 53 and the control valve 53 is manipulated in response thereto.

Signal 54, which is provided from computer 100 as the set point input to the flow controller 48, is representative of the flow rate of the acid-containing stream flowing through conduit means 16 required to maintain a desired acid to hydrocarbon ratio in the reactor 11. In response to signals 54 and 47, the flow controller 48 provides an output signal 55 which is responsive to the difference between signals 54 and 47. Signal 55 is scaled so as to be representative of the position of the control valve 57, which is operably located in conduit means 16, required to maintain the actual flow rate of the acid-containing stream flowing through conduit means 16 substantially equal to the desired flow rate represented by signal 54. Signal 55 is provided from the flow controller 48 as a control signal to the control valve 57 and the control valve 57 is manipulated in response thereto.

Referring now to the manner in which the control signals 51 and 54 are derived, signal 29, which is representative of the actual percentage of olefins in the feed stream flowing through conduit means 14, is provided as an input to the multiplying block 61. Signal 44, which is representative of the actual flow rate of the olefin-containing feed stream flowing through conduit means 14, is also provided as an input to the multiplying block 61 and as an input to the summing block 63. A set point signal 64, which is representative of the desired isobutane to olefin ratio in the feed stream flowing through conduit means 15 is also supplied as an input to the multiplying block 61 and as an input to the controller block 65. In general, the desired isobutane to olefin ratio for the feed stream flowing through conduit means 15 will be well known for a particular alkylation process and can be entered by the operator.

Signals 29, 44 and 64 are multiplied to establish signal 67 which is representative of the flow rate of isobutane through conduit means 12 required to maintain the actual isobutane to olefin ratio in the feed stream flowing through conduit means 15 substantially equal to the desired isobutane to olefin ratio represented by signal 64. Essentially, multiplying signals 29 and 44 gives the actual flow rate of olefins through conduit means 14 and multiplying this value by the isobutane to olefin ratio represented by signal 64 gives the required isobutane flow rate. Signal 67 is provided from the multiplying block 61 to the numerator input of the dividing block 69.

Signal 23, which is representative of the percentage of the isobutane-containing stream flowing through conduit means 12 which is isobutane, is provided to the denominator of the dividing block 69. Signal 67 is divided by signal 23 to establish signal 71 which is representative of the flow rate of the isobutane-containing stream flowing through conduit means 12 required to maintain the actual isobutane to olefin ratio in the feed stream flowing through conduit means 15 substantially equal to the desired isobutane to olefin ratio represented by signal 64. Signal 71 is provided from the dividing block 69 as an input to the summing block 72. Essentially, signal 71 may be considered a feed forward control signal because signal 71 is based on actual measurements of flow rates and actual analysis of the two fluid streams which make up feed stream flowing through conduit means 15.

Signal 33, which is representative of the actual isobutane to olefin ratio in the feed stream flowing through conduit means 15 is provided as the process variable input to the controller block 65. In response to signals 64 and 33, the controller block 65 provides an output signal 74 which is responsive to the difference between signals 33 and 64. Signal 74 is scaled so as to be representative of any change in the flow rate represented by signal 71 required to make the actual analysis represented by signal 33 substantially equal to the set point signal represented by signal 64.

It is noted that the actual analysis represented by signal 33 would be available periodically with a time interval between measurements of about 15 minutes being typical. Thus, signal 74 may be considered a feed back or trim factor. Essentially, if the feed forward control based on signal 71 is maintaining a desired isobutane to olefin ratio in the feed stream flowing through conduit means 15, signal 74 will have a magnitude of 0. Only when the feed forward control does not maintain the desired isobutane to olefin ratio will the trim factor represented by signal 74 become effective. Signal 74 is provided from the controller block 65 as a second input to the summing block 72. Signals 71 and 74 are summed to establish signal 51 which is provided as a control signal from computer 100 and which is utilized as previously described.

It would be possible to control the isobutane to olefin ratio based only on the analysis of the actual isobutane to olefin ratio provided by the analyzer transducer 31. However, the advantage of using two additional analyzer transducers 21 and 26 in the present invention lies in the fact that it takes about fifteen minutes for analyzer transducer 31 to establish the actual ratio based on the range of the analysis required. However, the percentages established by analyzer transducers 21 and 26 can be established much more quickly because it is easier to look at the impurities, which are generally known, and analyze these than to perform a full range analysis on the olefins. Thus, the feed forward control of the present invention based on the percentage analysis provided by analyzer transducers 21 and 26 is a particular advantage of the present invention.

Signal 38, which is representative of the actual flow rate of the isobutane-containing stream flowing through conduit means 12, is provided as second input to the summing block 63. Signals 38 and 44 are summed to establish signal 81 which is representative of the actual flow rate of the feed stream flowing through conduit means 15. Signal 81 is provided from the summing block 63 as an input to the summing block 82.

Signal 47, which is representative of the actual flow rate of the acid-containing stream flowing through conduit means 16, is provided as an input to the multiplying block 84 and as an input to the multiplying block 85. Signal 86, which is representative of the percentage of the acid-containing stream flowing through conduit means 16 which is acid, is provided as a second input to the multiplying block 84 and is provided to the subtrahend input of the subtracting block 87. In the present invention, signal 86 is preferably an operator entered value based on an operator's knowledge of the alkylation process. Preferably, an analyzer would be utilized to supply signal 86 but there are presently no commercially available analyzers capable of analyzing the acid containing stream flowing through conduit means 16 due to its severe corrosive nature. At such time as such an analyzer becomes available, it would be preferred to use a chromatographic analyzer to establish signal 86.

Signal 47 is multiplied by signal 86 to establish signal 88 which is representative of the actual flow rate of acid to the reactor 11. Signal 88 is provided from the multiplying block 84 as the process variable input to the controller block 89.

Signal 91, which is representative of 100%, is supplied to the minuend input of the subtracting block 87. Signal 86 is subtracted from signal 91 to establish signal 92 which is representative of the percentage of the acid-containing stream flowing through conduit means 16 which is hydrocarbon. Signal 92 is provided from the subtracting block 87 as a second input to the multiplying block 85.

Signal 47 is multiplied by signal 92 to establish signal 93 which is representative of the actual flow rate of hydrocarbons through conduit means 16. Signal 93 is provided from the multiplying block 85 as an input to the summing block 82. Signal 93 is summed with signal 81 to establish signal 94 which is representative of the hydrocarbon flow rate to the alkylation reactor 11. Signal 94 is provided from the summing block 82 as an input to the multiplying block 95. Signal 96, which is an operator entered value representative of the desired acid to hydrocarbon ratio in the alkylation reactor 11, is also supplied to the multiplying block 95. Typically, the desired acid to hydrocarbon ratio for any particular alkylation reactor will be well known. Signal 94 is multiplied by signal 96 to establish signal 97 which is representative of the flow rate of acid through conduit means 16 required to maintain a desired acid to hydrocarbon ratio in the alkylation reactor 11. Signal 97 is provided as the set point input to the controller block 89.

In response to signals 88 and 97, the controller block 89 provides an output signal 54 which is responsive to the difference between signals 88 and 97. Signal 54 is provided as an output from computer 100 and is utilized as has been previously described.

Essentially, the control system illustrated in FIG. 1 compensates for the fact that the olefin-containing stream flowing through conduit means 14 will typically not be 100% olefins and the isobutane-containing stream flowing through conduit means 12 will typically not be 100% isobutane in effecting the control of the isobutane to olefin ratio in the feed flowing through conduit means 15. Also, the fact that the acid-containing stream flowing through conduit means 16 will typically not be 100% acid and indeed will generally contain hydrocarbons, is compensated for in the control of the acid to hydrocarbon ratio in the reactor 11. This control results in a desired ratio of reactants in the reactor 11 which results in improved performance of the alkylation process.

It is noted that the isobutane to olefin ratio control and the acid to hydrocarbon ratio control may be used separately but it is presently preferred to use the two ratio controls in combination.

Referring now to FIG. 2, there is illustrated parallel alkylation reactors 111 and 112. In general, each of the alkylation reactors 111 and 112 would have the control system illustrated in FIG. 1 associated therewith. Also, only the process streams needed to illustrate the load balancing control of the present invention are illustrated in FIG. 2. The control systems of FIGS. 1 and 2 were not combined for the sake of simplicity in describing the present invention.

An olefins-containing stream flowing through conduit means 114 is split between conduit means 115 and 116 and is thus provided to reactors 112 and 111 respectively. Reactants are removed from reactor 112 through conduit means 117. In like manner, reactants are removed from reactor 111 through conduit means 118.

Again, process measurements are made and supplied to computer 100. In response to these process measurements and operator supplied set point signals, computer 100 provides two output control signals. Again, the process measurements will be described and the use of the two output control signals will be described. This description will be followed by a detailed description of the manner in which the process measurements are utilized to derive the two control signals.

Temperature transducer 121 in combination with a temperature sensing device such as a thermocouple, which is operably located in conduit means 117, provides an output signal 122 which is representative of the temperature of the reactants flowing through conduit means 117. Signal 122 is provided as an input to computer 100. In like manner, temperature transducer 124 provides an output signal 125, which is representative of the temperature of the reactants flowing through conduit means 118, to computer 100.

Pressure transducer 126 in combination with a pressure sensing device, which is operably located in conduit means 114, provides an output signal 127 which is representative of the actual pressure of the olefin-containing feed stream flowing through conduit means 114. Signal 127 is provided from the pressure transducer 126 as an input to computer 100.

Balancing of the load between reactors 111 and 112 is generally obtained when the temperature of the reactants flowing through conduit means 117 and 118 are equal. If one reactor is hotter than the other reactor, the hotter reactor will generally result in a poor quality and yield of alkylate. Therefore, it is desirable to maintain the temperature of the reactants flowing through conduit means 117 and 118 substantially equal.

In response to the described measurements and operator entered set points, computer 100 provides two output control signals. Signal 131, which is representative of the flow rate of the olefin-containing stream flowing through conduit means 115 required to maintain the actual temperature of the reactants flowing through conduit means 117 substantially equal to the actual temperature of the reactants flowing through conduit means 118, is provided as a set point signal to the flow controller 132. Flow transducer 134 in combination with the flow sensor 135, which is operably located in conduit means 115, provides an output signal 136 which is representative of the actual flow rate of the olefin-containing stream flowing through conduit means 115. Signal 136 is provided from the flow transducer 134 as the process variable input to the flow controller 132. In response to signals 131 and 136, the flow controller 132 proviees an output signal 137 which is responsive to the difference between signals 131 and 136. Signal 137 is scaled so as to be representative of the position of the control valve 138, which is operably located in conduit means 115, required to maintain the actual flow rate of the olefin-containing stream flowing through conduit means 115 substantially equal to the desired flow rate represented by signal 131. Signal 137 is provided as a control signal from the flow controller 132 to the control valve 138 and the control valve 138 is manipulated in response thereto.

Signal 141, which is representative of the flow rate of the olefin-containing stream flowing through conduit means 116 required to maintain the actual pressure of the olefin-containing stream flowing through conduit means 114 substantially equal to the desired pressure of the olefin-containing stream flowing through conduit means 114, is provided as a set point signal to the flow controller 142. Flow transducer 144 in combination with the flow sensor 145, which is operably located in conduit means 116, provides an output signal 146 which is representative of the actual flow rate of the olefin-containing stream flowing through conduit means 116. Signal 146 is provided from the flow transducer 144 as the process variable input to the flow controller 142. In response to signals 141 and 146, the flow controller 142 provides an output signal 147 which is responsive to the difference between signals 141 and 146. Signal 147 is scaled so as to be representative of the position of the control valve 148, which is operably located in conduit means 116, required to maintain the actual flow rate of the olefin-containing stream flowing through conduit means 116 substantially equal to the desired flow rate represented by signal 141. Signal 147 is provided as a control signal from the flow controller 142 to the control valve 148 and the control valve 148 is manipulated in response thereto.

Referring now to the manner in which the process measurements are utilized to generate the control signals 131 and 141, signal 122, which is representative of the temperature of the reactants flowing through conduit means 117 is provided to the minuend input of the subtracting block 151. Signal 125, which is representative of the temperature of the reactants flowing through conduit means 118 is provided to the subtrahend input of the subtracting block 151. Signal 125 is subtracted from signal 122 to establish signal 153 which is representative of any difference between the temperature represented by signal 122 and the temperature represented by signal 125. Signal 153 is provided as the process variable input to the controller block 154. Signal 156, which is representative of the desired difference between the temperature of the reactants flowing through conduit means 117 and the reactants flowing through conduit means 118 (in the present case zero) is supplied as a set point signal to the controller block 154. In response to signals 153 and 156, the controller block 154 establishes signal 131 which is responsive to the difference between signals 153 and 156. Signal 131 is provided as an output control signal from computer 100 and is utilized as has been previously described.

Signal 127, which is representative of the actual pressure of the olefin-containing stream flowing through conduit means 114, is provided as the process variable input to the controller block 161. Controller block 161 is also provided with a set point signal 162 which is representative of the desired pressure for the olefin-containing stream flowing through conduit means 114. In response to signals 127 and 162, the controller block 161 establishes signal 141 which is responsive to the difference between signals 127 and 162. Signal 141 is provided as an output control signal from computer 100 and is utilized as has been previously described.

Use of a comparison of the temperatures of the reactants flowing through conduit means 117 and 118 to control the flow rate of the olefins flowing through conduit means 115 provides for balancing of the load on reactors 111 and 112. Use of the pressure control to manipulate the flow rate of the olefin-containing stream flowing through conduit means 116 provides for smooth operation and a constant inlet pressure.

It is noted that use of the reactor balancing control illustrated in FIG. 2 is not required in conjunction with the control illustrated in FIG. 1 but is preferred where two or more parallel alkylation reactors are employed in an alkylation process.

The invention has been described in terms of a presently preferred embodiment as illustrated in FIGS. 1 and 2. Specific components which can be used in the practice of the invention as illustrated in FIGS. 1 and 2 such as flow sensors 37, 42, 46, 135 and 145; flow transducers 36, 41, 45, 134 and 144; flow controllers 39, 48, 132 and 142; control valves 53, 57, 138 and 148; temperature transducers 121 and 124; and pressure transducer 126 are each well known, commercially available control compnents such as are described at length in Perry's *Chemical Engineers Handbook,* 4th Edition, Chapter 22, McGraw-Hill.

While the invention has been described in terms of the presently preferred embodiment, reasonable variations and modifications are possible by those skilled in the art and such variations and modifications are within the scope of the described invention and the appended claims.

That which is claimed is:

1. Apparatus comprising:
    a first alkylation reactor;
    means for combining an isoparaffin-containing first fluid stream with an olefin-containing second fluid stream to form a combined feed stream and for providing said combined feed stream to said first alkylation reactor;
    means for providing a third fluid stream containing an acid which is suitable for catalyzing an alkylation reaction to said first alkylation reactor;
    means for establishing a first signal representative of the desired isoparaffin to olefin ratio in said combined feed stream;
    means for establishing a second signal representative of the actual percentage of said second fluid stream which is olefins based on an analysis of the components of said second fluid stream which are not olefins;
    means for establishing a third signal representative of the flow rate of said second fluid stream;
    means for multiplying said first, second and third signals to establish a fourth signal which is representative of the flow rate of isoparaffin in said first fluid stream required to maintain the actual isoparaffin to olefin ratio in said combined feed stream substantially equal to the desired isoparaffin to olefin ratio represented by said first signal;
    means for establishing a fifth signal representative of the actual percentage of said first fluid stream which is isoparaffin based on an analysis of the components of said first fluid stream which are not isoparaffin;
    means for dividing said fourth signal by said fifth signal to establish a sixth signal which is representative of the actual flow rate of said first fluid stream required to maintain the actual isoparaffin to olefin ratio in said combined feed stream substantially equal to the desired isoparaffin to olefin ratio represented by said first signal; and
    means for manipulating the flow rate of said first fluid stream in response to said sixth signal to thereby maintain the actual isoparaffin to olefin ratio in said combined feed stream substantially equal to the desired ratio represented by said first signal.

2. Apparatus in accordance with claim 1 additionally comprising:
    means for establishing a seventh signal representative of the actual isoparaffin to olefin ratio in said combined feed stream;
    means for comparing said first signal and said seventh signal and for establishing an eighth signal which is responsive to the difference between said first signal and said seventh signal, wherein said eighth signal is scaled so as to be representative of any changes in the magnitude of said sixth signal required to maintain the actual isoparaffin to olefin ratio represented by said seventh signal substantially equal to the desired isoparaffin to olefin ratio represented by said first signal; and
    means for combining said eighth signal and said sixth signal, wherein said sixth signal as modified by said eighth signal is utilized to manipulate the flow rate of said first fluid stream.

3. Apparatus in accordance with claim 1 additionally comprising:
    means for establishing a seventh signal representative of the flow rate of acid in said third fluid stream;
    means for establishing an eighth signal representative of the flow rate of hydrocarbons in said third fluid stream;
    means for establishing a ninth signal representative of the flow rate of said combined feed stream;
    means for summing said eighth signal and said ninth signal to establish a tenth signal which is representative of the total flow rate of hydrocarbons to said first alkylation reactor;
    means for establishing an eleventh signal representative of the desired acid to hydrocarbon ratio in said first alkylation reactor;
    means for multiplying said tenth signal and said eleventh signal to establish a twelfth signal representative of the flow rate of acid in said third fluid stream required to maintain the desired acid to hydrocarbon ratio represented by said eleventh signal;
    means for comparing said seventh signal and said twelfth signal and for establishing a thirteenth signal which is responsive to the difference between said seventh signal and said twelfth signal; and
    means for manipulating the flow rate of said third fluid stream in response to said thirteenth signal to thereby maintain the actual acid to hydrocarbon ratio in said first alkylation reactor substantially equal to the desired ratio represented by said eleventh signal.

4. Apparatus in accordance with claim 1 or claim 3 additionally comprising:
    means for withdrawing a reactant-containing fourth stream from said first alkylation reactor;
    a second alkylation reactor;
    means for splitting an olefin-containing fifth fluid stream into said second fluid stream and a sixth fluid stream;
    means for providing said sixth fluid stream to said second alkylation reactor;
    means for withdrawing a reactant-containing seventh fluid stream from said second alkylation reactor;
    means for establishing a fourteenth signal representative of the actual difference between the temperature of said fourth fluid stream and the temperature of said seventh fluid stream;
    means for establishing a fifteenth signal representative of any desired difference between the temperature of said fourth fluid stream and said seventh fluid stream;

means for comparing said fourteenth signal and said fifteenth signal and for establishing a sixteenth signal which is responsive to the difference between said fourteenth signal and said fifteenth signal; and means for manipulating the flow rate of said second fluid stream in response to said sixteenth signal to thereby balance the load on said first and second alkylation reactors.

5. Apparatus in accordance with claim 3 wherein said means for establishing said seventh signal comprises:

means for establishing a fourteenth signal representative of the actual flow rate of said third fluid stream;

means for establishing a fifteenth signal representative of the percentage of said third fluid stream which is acid; and means for multiplying said fourteenth and fifteenth signals to establish said seventh signal.

6. Apparatus in accordance with claim 5 wherein said means for establishing said eighth signal comprises:

means for subtracting said fifteenth signal from one hundred percent to establish a sixteenth signal; and means for multiplying said fourteenth signal by said sixteenth signal to establish said eighth signal.

7. Apparatus in accordance with claim 4 wherein said means for establishing said fourteenth signal comprises:

means for establishing a seventeenth signal representative of the actual temperature of said fourth fluid stream;

means for establishing an eighteenth signal representative of the actual temperature of said seventh fluid stream; and means for subtracting said eighteenth signal from said seventeenth signal to establish said fourteenth signal.

8. Apparatus in accordance with claim 4 additionally comprising:

means for establishing a seventeenth signal representative of the actual pressure of said fifth fluid stream;

means for establishing an eighteenth signal representative of the desired pressure of said fifth fluid stream;

means for comparing said seventeenth signal and said eighteenth signal and for establishing a nineteenth signal which is responsive to the difference between said seventeenth signal and said eighteenth signal; and means for manipulating the flow rate of said sixth fluid stream in response to said nineteenth signal.

9. Apparatus comprising:

a first alkylation reactor;

means for combining an isoparaffin-containing first fluid stream with an olefin-containing second fluid stream to form a combined feed stream and for providing said combined feed stream to said first alkylation reactor;

means for providing a third fuid stream containing an acid which is suitable for catalyzing an alkylation reaction to said first alkylation reactor;

means for establishing a first signal representative of the flow rate of acid in said third fluid stream;

means for establishing a second signal representative of the flow rate of hydrocarbons in said third fluid stream;

means for establishing a third signal representative of the flow rate of said combined feed stream;

means for summing said second signal and said third signal to establish a fourth signal which is representative of the total flow rate of hydrocarbons to said first alkylation reactor;

means for establishing a fifth signal representative of the desired acid to hydrocarbon ratio in said first alkylation reactor;

means for multiplying said fourth signal and said fifth signal to establish a sixth signal representative of the flow rate of acid in said third fluid stream required to maintain the desired acid to hydrocarbon ratio represented by said fifth signal;

means for comparing said first signal and said sixth signal and for establishing a seventh signal which is responsive to the difference between said first signal and said sixth signal; and means for manipulating the flow rate of said third fluid stream in response to said seventh signal to thereby maintain the actual acid to hydrocarbon ratio in said first alkylation reactor substantially equal to the desired ratio represented by said fifth signal.

10. Apparatus in accordance with claim 9 wherein said means for establishing said first signal comprises:

means for establishing an eighth signal representative of the actual flow rate of said third fluid stream;

means for establishing a ninth signal representative of the percentage of said third fluid stream which is acid; and means for multiplying said eighth and ninth signals to establish said first signal.

11. Apparatus in accordance with claim 9 additionally comprising:

means for withdrawing a reactant-containing fourth stream from said first alkylation reactor;

a second alkylation reactor;

means for splitting an olefin-containing fifth fluid stream into said second fluid stream and a sixth fluid stream;

means for providing said sixth fluid stream to said second alkylation reactor;

means for withdrawing a reactant-containing seventh fluid stream from said second alkylation reactor;

means for establishing an eighth signal representative of the actual difference between the temperature of said fourth fluid stream and the temperature of said seventh fluid stream;

means for establishing a ninth signal representative of any desired difference between the temperature of said fourth fluid stream and said seventh fluid stream;

means for comparing said eighth signal and said ninth signal and for establishing a tenth signal which is responsive to the difference between said eighth signal and said ninth signal; and means for manipulating the flow rate of said second fluid stream in response to said tenth signal.

12. Apparatus in accordance with claim 10 wherein said means for establishing said second signal comprises:

means for subtracting said ninth signal from one hundred percent to establish a tenth signal; and means for multiplying said eighth signal by said tenth signal to establish said second signal.

13. Apparatus in accordance with claim 11 wherein said means for establishing said eighth signal comprises:

means for establishing an eleventh signal representative of the actual temperature of said fourth fluid stream;

means for establishing a twelfth signal representative of the actual temperature of said seventh fluid stream; and means for subtracting said twelfth signal from said eleventh signal to establish said eighth signal.

14. Apparatus in accordance with claim 11 additionally comprising:

means for establishing an eleventh signal representative of the actual pressure of said fifth fluid stream;

means for establishing a twelfth signal representative of the desired pressure of said fifth fluid stream;

means for comparing said eleventh signal and said twelfth signal and for establishing a thirteenth signal which is responsive to the difference between said eleventh signal and said twelfth signal; and means for manipulating the flow rate of said sixth fluid stream in response to said thirteenth signal.

15. Apparatus comprising:

a first alkylation reactor;

a second alkylation reactor;

means for splitting an olefin-containing first fluid stream into a second fluid stream and a third fluid stream;

means for providing said second fluid stream to said first alkylation reactor;

means for providing said third fluid stream to said second alkylation reactor;

means for withdrawing a reactant-containing fourth fluid stream from said first alkylation reactor;

means for withdrawing a reactant-containing fifth fluid stream from said second alkylation reactor;

means for establishing a first signal representative of the actual difference between the temperature of said fourth fluid stream and the temperature of said fifth fluid stream;

means for establishing a second signal representative of any desired difference between the temperature of said fourth fluid stream and said fifth fluid stream;

means for comparing said first signal and said second signal and for establishing a third signal which is responsive to the difference between said first signal and said second signal; and means for manipulating the flow rate of said second fluid stream in response to said third signal to thereby balance the load on said first and second alkylation reactors.

16. Apparatus in accordance with claim 15 wherein said means for establishing said first signal comprises:

means for establishing a fourth signal representative of the actual temperature of said fourth fluid stream;

means for establishing a fifth signal representative of the actual temperature of said fifth fluid stream; and means for subtracting said fifth signal from said fourth signal to establish said first signal.

17. Apparatus in accordance with claim 15 additionally comprising:

means for establishing a fourth signal representative of the actual pressure of said first fluid stream;

means for establishing a fifth signal representative of the desired pressure of said first fluid stream;

means for comparing said fourth signal and said fifth signal and for establishing a sixth signal which is responsive to the difference between said fourth signal and said fifth signal; and means for manipulating the flow rate of said third fluid stream in response to said sixth signal.

18. A method for controlling a first alkylation reactor, wherein a isoparaffin-containing first fluid stream is combined with an olefin-containing second fluid stream to form a combined feed stream with the combined feed stream being provided to said first alkylation reactor and wherein a third fluid stream containing an acid which is suitable for catalyzing an alkylation reaction is provided to said first alkylation reactor, said method comprising the steps of:

establishing a first signal representative of the desired isoparaffin to olefin ratio in said combined feed stream;

establishing a second signal representative of the actual percentage of said second fluid stream which is olefins based on an analysis of the components of said second fluid stream which are not olefins;

establishing a third signal representative of the flow rate of said second fluid stream;

multiplying said first, second and third signals to establish a fourth signal which is representative of the flow rate of isoparaffin in said first fluid stream required to maintain the actual isoparaffin to olefin ratio in said combined feed stream substantially equal to the desired isoparaffin to olefin ratio represented by said first signal;

establishing a fifth signal representative of the actual percentage of said first fluid stream which is isoparaffin based on an analysis of the components of said first fluid stream which are not isoparaffin;

dividing said fourth signal by said fifth signal to establish a sixth signbal which is representative of the actual flow rate of said first fluid stream required to maintain the actual isoparaffin to olefin ratio in said combined feed stream substantially equal to the desired isoparaffin to olefin ratio represented by said first signal; and manipulating the flow rate of said first fluid stream in response to said sixth signal to thereby maintain the actual isoparaffin to olefin ratio in said combined feed stream substantially equal to the desired ratio represented by said first signal.

19. A method in accordance with claim 18 additionally comprising the steps of:

establishing a seventh signal representative of the actual isoparaffin to olefin ratio in said combined feed stream;

comparing said first signal and said seventh signal and establishing an eighth signal which is responsive to the difference between said first signal and said seventh signal, wherein said eighth signal is scaled so as to be representative of any changes in the magnitude of said sixth signal required to maintain the actual isoparaffin to olefin ratio represented by said seventh signal substantially equal to the desired isoparaffin to olefin ratio represented by said first signal; and combining said eighth signal and said sixth signal, wherein said sixth signal as modified by said eighth signal is utilized to manipulate the flow rate of said first fluid stream.

20. A method in accordance with claim 18 additionally comprising the steps of:

establishing a seventh signal representative of the flow rate of acid in said third fluid stream;

establishing an eighth signal representative of the flow rate of hydrocarbons in said third fluid stream;

establishing a ninth signal representative of the flow rate of said combined feed stream;

summing said eighth signal and said ninth signal to establish a tenth signal which is representative of the total flow rate of hydrocarbons to said first alkylation reactor;

establishing an eleventh signal representative of the desired acid to hydrocarbon ratio in said first alkylation reactor;

multiplying said tenth signal and said eleventh signal to establish a twelfth signal representative of the flow rate of acid in said third fluid stream required to maintain the desired acid to hydrocarbon ratio represented by said eleventh signal;

comparing said seventh signal and said twelfth signal and establishing a thirteenth signal which is responsive to the difference between said seventh signal and said twelfth signal; and manipulating the flow rate of said third fluid stream in response to said thirteenth signal to thereby maintain the actual acid to hydrocarbon ratio in said first alkylation reactor substantially equal to the desired ratio represented by said eleventh signal.

21. A method in accordance with claim 20 wherein said step of establishing said seventh signal comprises:

establishing a fourteenth signal representative of the actual flow rate of said third fluid stream;

establishing a fifteenth signal representative of the percentage of said third fluid stream which is acid; and multiplying said fourteenth and fifteenth signals to establish said seventh signal.

22. A method in accordance with claim 18 or claim 20 for controlling loading on said first alkylation reactor and a second alkylation reactor, wherein a reactant-containing fourth fluid stream is withdrawn from said first alkylation reactor, wherein an olefin-containing fifth fluid stream is split into said second fluid stream and a sixth fluid stream with said sixth fluid stream being provided to said second alkylation reactor and wherein a reactant-containing seventh fluid stream is withdrawn from said second alkylation reactor, said method for controlling the loading on said first alkylation reactor and said second alkylation reactor comprising the steps of:

establishing a fourteenth signal representative of the actual difference between the temperature of said fourth fluid stream and the temperature of said seventh fluid stream;

establishing a fifteenth signal representative of any desired difference between the temperature of said fourth fluid stream and said seventh fluid stream;

comparing said fourteenth signal and said fifteenth signal and establishing a sixteenth signal which is responsive to the difference between said fourteenth signal and said fifteenth signal; and manipulating the flow rate of said second fluid stream in response to said sixteenth signal to thereby balance the load on said first and second alkylation reactors.

23. A method in accordance with claim 21 wherein said step of establishing said eighth signal comprises:

subtracting said fifteenth signal from one hundred percent to establish a sixteenth signal; and multiplying said fourteenth signal by said sixteenth signal to establish said eighth signal.

24. A method in accordance with claim 22 wherein said step of establishing said fourteenth signal comprises:

establishing a seventeenth signal representative of the actual temperature of said fourth fluid stream;

establishing an eighteenth signal representative of the actual temperature of said seventh fluid stream; and subtracting said eighteenth signal from said seventeenth signal to establish said fourteenth signal.

25. A method in accordance with claim 22 additionally comprising the steps of:

establishing a seventeenth signal representative of the actual pressure of said fifth fluid stream;

establishing an eighteenth signal representative of the desired pressure of said fifth fluid stream;

comparing said seventeenth signal and said eighteenth signal and establishing a nineteenth signal which is responsive to the difference between said seventeenth signal and said eighteenth signal; and manipulating the flow rate of said sixth fluid stream in response to said nineteenth signal.

26. A method for controlling a first alkylation reactor, wherein an isoparaffin-containing first fluid stream is combined with an olefin-containing second fluid stream to form a combined feed stream with the combined feed stream being provided to said first alkylation reactor and wherein a third fluid stream containing an acid which is suitable for catalyzing an alkylation reaction is provided to said first alkylation reactor, said method comprising the steps of:

establishing a first signal representative of the flow rate of acid in said third fluid stream;

establishing a second signal representative of the flow rate of hydrocarbons in said third fluid stream;

establishing a third signal representative of the flow rate of said combined feed stream;

summing said second signal and said third signal to establish a fourth signal which is representative of the total flow rate of hydrocarbons to said first alkylation reactor;

establishing a fifth signal representative of the desired acid to hydrocarbon ratio in said first alkylation reactor;

multiplying said fourth signal and said fifth signal to establish a sixth signal representative of the flow rate of acid in said third fluid stream required to maintain the desired acid to hydrocarbon ratio represented by said fifth signal;

comparing said first signal and said sixth signal and establishing a seventh signal which is responsive to the difference between said first signal and said sixth signal; and manipulating the flow rate of said third fluid stream in response to said seventh signal to thereby maintain the actual acid to hydrocarbon ratio in said first alkylation reactor substantially equal to the desired ratio represented by said fifth signal.

27. A method in accordance with claim 26 wherein said step of establishing said first signal comprises:

establishing an eighth signal representative of the actual flow rate of said third fluid stream;

establishing a ninth signal representative of the percentage of said third fluid stream which is acid; and multiplying said eighth and ninth signals to establish said first signal.

28. A method in accordance with claim 26 for controlling loading on said first alkylation reactor and a second alkylation reactor, wherein a reactant-containing fourth fluid stream is withdrawn from said first alkylation reactor, an olefin-containing fifth fluid stream is split into said second fluid stream and a sixth fluid stream with said sixth fluid stream being provided to said second alkylation reactor and wherein a reactant-containing seventh fluid stream is withdrawn from said second alkylation reactor, said method for controlling the loading on said first alkylation reactor and said second alkylation reactor comprising the steps of:
   establishing an eighth signal representative of the actual difference between the temperature of said fourth fluid stream and the temperature of said seventh fluid stream;
   establishing a ninth signal representative of any desired difference between the temperature of said fourth fluid stream and said seventh fluid stream;
   comparing said eighth signal and said ninth signal and establishing a tenth signal which is responsive to the difference between said eighth signal and said ninth signal; and
   manipulating the flow rate of said second fluid stream in response to said tenth signal.

29. A method in accordance with claim 27 wherein said step of establishing said second signal comprises:
   subtracting said ninth signal from one hundred percent to establish a tenth signal; and
   multiplying said eighth signal by said tenth signal to establish said second signal.

30. A method in accordance with claim 28 wherein said step of establishing said eighth signal comprises:
   establishing an eleventh signal representative of the actual temperature of said fourth fluid stream;
   establishing a twelfth signal representative of the actual temperature of said seventh fluid stream; and
   subtracting said twelfth signal from said eleventh signal to establish said eighth signal.

31. A method in accordance with claim 28 additionally comprising the steps of:
   establishing an eleventh signal representative of the actual pressure of said fifth fluid stream;
   establishing a twelfth signal representative of the desired pressure of said fifth fluid stream;
   comparing said eleventh signal and said twelfth signal and establishing a thirteenth signal which is responsive to the difference between said eleventh signal and said twelfth signal; and
   manipulating the flow rate of said sixth fluid stream in response to said thirteenth signal.

32. A method for controlling first and second alkylation reactors, wherein an olefin-containing first fluid stream is split into a second fluid stream and a third fluid stream with said second fluid stream being provided as a feed to said first alkylation reactor and said third fluid stream being provided as a feed to said second alkylation reactor, wherein a reactant-containing fourth fluid stream is withdrawn from said first alkylation reactor and wherein a reactant-containing fifth fluid stream is withdrawn from said second alkylation reactor, said method comprising the steps of:
   establishing a first signal representative of the actual difference between the temperature of said fourth fluid stream and the temperature of said fifth fluid stream;
   establishing a second signal representative of any desired difference between the temperature of said fourth fluid stream and said fifth fluid stream;
   comparing said first signal and said second signal and establishing a third signal which is responsive to the difference between said first signal and said second signal; and
   manipulating the flow rate of said second fluid stream in response to said third signal to thereby balance the load on said first and second alkylation reactors.

33. A method in accordance with claim 32 wherein said step of establishing said first signal comprises:
   establishing a fourth signal representative of the actual temperature of said fourth fluid stream;
   establishing a fifth signal representative of the actual temperature of said fifth fluid stream; and
   subtracting said fifth signal from said fourth signal to establish said first signal.

34. A method in accordance with claim 32 additionally comprising the step of:
   establishing a fourth signal representative of the actual pressure of said first fluid stream;
   establishing a fifth signal representative of the desired pressure of said first fluid stream;
   comparing said fourth signal and said fifth signal and establishing a sixth signal which is responsive to the difference between said fourth signal and said fifth signal; and
   manipulating the flow rate of said third fluid stream in response to said sixth signal.

* * * * *